(12) United States Patent
Kim et al.

(10) Patent No.: US 10,920,248 B2
(45) Date of Patent: Feb. 16, 2021

(54) METHOD FOR MASS-PRODUCING VINIFERIN USING STEVIOSIDE FROM CELL CULTURE OF GRAPEVINE TISSUE

(71) Applicant: KOREA RESEARCH INSTITUTE OF BIOSCIENCE AND BIOTECHNOLOGY, Daejeon (KR)

(72) Inventors: Cha Young Kim, Daejeon (KR); Yu Jeong Jeong, Daejeon (KR); Suk Weon Kim, Daejeon (KR); Mun Chual Rho, Daejeon (KR); Young Bae Ryu, Daejeon (KR); Woo Song Lee, Daejeon (KR); Jae Cheol Jeong, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 16/084,445

(22) PCT Filed: Feb. 28, 2017

(86) PCT No.: PCT/KR2017/002187
§ 371 (c)(1),
(2) Date: Sep. 12, 2018

(87) PCT Pub. No.: WO2017/160010
PCT Pub. Date: Sep. 21, 2017

(65) Prior Publication Data
US 2019/0078122 A1   Mar. 14, 2019

(30) Foreign Application Priority Data
Mar. 14, 2016   (KR) .................... 10-2016-0030510

(51) Int. Cl.
| | | |
|---|---|---|
| *A01H 4/00* | (2006.01) | |
| *C12N 5/04* | (2006.01) | |
| *C12P 7/22* | (2006.01) | |
| *C12P 17/04* | (2006.01) | |
| *A01H 3/04* | (2006.01) | |
| *C12N 5/00* | (2006.01) | |

(52) U.S. Cl.
CPC .............. *C12P 7/22* (2013.01); *A01H 3/04* (2013.01); *A01H 4/00* (2013.01); *A01H 4/005* (2013.01); *C12N 5/0025* (2013.01); *C12N 5/04* (2013.01); *C12P 17/04* (2013.01)

(58) Field of Classification Search
CPC ... C12P 17/04; C12P 7/22; A01H 4/00; A01H 4/005; C12N 5/0025; C12N 5/04
USPC .................. 435/469, 419, 468, 420
See application file for complete search history.

(56) References Cited

U.S. PATENT DOCUMENTS

| | | | |
|---|---|---|---|
| 7,799,357 B2 | 9/2010 | Ho et al. | |
| 8,551,507 B2 * | 10/2013 | Liu ................... | A61K 31/7048 424/400 |
| 2014/0147886 A1 | 5/2014 | Medina-Bolivar et al. | |

FOREIGN PATENT DOCUMENTS

| | | | | |
|---|---|---|---|---|
| EP | 2735609 | * | 5/2014 | |
| EP | 2735609 A2 | * | 5/2014 | ............... C12N 5/00 |
| EP | 2735609 A2 | | 5/2014 | |
| EP | 2256209 B1 | | 4/2016 | |
| KR | 10-2003-0021976 A | | 3/2003 | |
| KR | 10-2005-0089492 A | | 9/2005 | |

OTHER PUBLICATIONS

Davidov-Pardo, Gabriel et al.: "Resveratrol Encapsulation: Designing Delivery Systems to Overcome Solubility, Stability and Bioavailability Issues", Trends in Food Science & Technology, vol. 38, 2014, pp. 88-103.
Koga, Clarissa C: "Stabilization of Resveratrol through Microencapsulation and Incorporation into Food Products", Doctoral Thesi S, University of Illinois at Urbana-Champaign, 2015, chapters i-viii, pp. 1-151.
Santamaria, Anna Rita et al.: "Effects of Elicitors on the Production of Resveratrol and Viniferins in Cell Cultures of *Vitis vinifera* L. cv italia", Journal of Agricultural and Food Chemistry, vol. 59, Jul. 14, 2011 (Jul. 14, 2011), pp. 9094-9101.
Cantos, Emma et al: "Postharvest Stilbene-Enrichment of Red and White Table Grape Varieties Using UV-C Irradiation Pulses", Journal of Agricultural and Food Chemistry. vol. 50, Sep. 24, 2002, pp. 3322-6329.
Anna Rita Santamaria et al., "Effects of Elicitors on the Production of Resveratrol and Viniferins in Cell Cultures of *Vitis vinifera* L. cv italia", Journal of Agricultural and Food Chemistry, Jul. 14, 2011, pp. 9094-9101.

\* cited by examiner

*Primary Examiner* — Keith O. Robinson
(74) *Attorney, Agent, or Firm* — Novick, Kim & Lee, PLLC; Jae Yoon Kim (57) ABSTRACT

The present invention relates to a method for mass-production of viniferin using stevioside from cell culture of grape tree tissue. Viniferin is known to be effective for protection of liver, anticancer, antioxidant, and skin whitening, have an effect of inhibiting oxidation of low-density lipoprotein and high-density lipoprotein and inhibiting the proliferation and migration of vascular smooth muscle cells. Therefore, the present invention is very useful for the mass production of viniferin among the useful substances (stilbene compounds) from a callus derived from the anther tissue of the grape plant, which is very important for the related industries.

3 Claims, 6 Drawing Sheets

Specification includes a Sequence Listing.

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: STS-F primer

<400> SEQUENCE: 1
atggcttcag ttgaggaaat caga                                    24

<210> SEQ ID NO 2
<211> LENGTH: 25
<212> TYPE: DNA
<213> ORGANISM: Artificial Sequence
<220> FEATURE:
<223> OTHER INFORMATION: STS-R primer

<400> SEQUENCE: 2
ttaatttgtc accataggaa tgcta                                   25

<210> SEQ ID NO 3
<211> LENGTH: 22
<212> TYPE: DNA
<213> ORGANISM: Artificial Sequence
<220> FEATURE:
<223> OTHER INFORMATION: ROMT-F primer

<400> SEQUENCE: 3
atggatttgg caaacggtgt ga                                      22

<210> SEQ ID NO 4
<211> LENGTH: 24
<212> TYPE: DNA
<213> ORGANISM: Artificial Sequence
<220> FEATURE:
<223> OTHER INFORMATION: ROMT-R primer

<400> SEQUENCE: 4
tcaaggataa acctcaatga ggga                                    24

<210> SEQ ID NO 5
<211> LENGTH: 20
<212> TYPE: DNA
<213> ORGANISM: Artificial Sequence
<220> FEATURE:
<223> OTHER INFORMATION: ACTIN-F primer

<400> SEQUENCE: 5
tgctgacaga atgagcaagg                                         20

<210> SEQ ID NO 6
<211> LENGTH: 26
<212> TYPE: DNA
<213> ORGANISM: Artificial Sequence
<220> FEATURE:
<223> OTHER INFORMATION: ACTIN-R primer

<400> SEQUENCE: 6
tactaagaag ctttcaaccc agtata                                  26

METHOD FOR MASS-PRODUCING VINIFERIN USING STEVIOSIDE FROM CELL CULTURE OF GRAPEVINE TISSUE

TECHNICAL FIELD

The present invention relates to a method for mass production of viniferin using stevioside from cell culture of grape tree tissue.

BACKGROUND ART

Stilbene is primarily expressed as a resveratrol compound and is a small class of plant secondary metabolites derived from the common phenylpropanoid pathway including phenylalanine initially. Resveratrol (3,4',5-transtrihydroxystilbene) is a naturally occurring phytoalexin produced in some plants such as grapes, peanuts, and berries in response to environmental stresses, for example, UV irradiation and fungi infections. Resveratrol and its derivatives play critical roles as phytoalexins and anti-oxidants in plant defense reactions as well as exhibit various beneficial properties including anti-cancer, anti-inflammatory, anti-tumor activity, and anti-aging effects.

Although the resveratrol, which shows anti-cancer and anti-oxidant activity, is a promising natural functional resource that has been confirmed as a promising candidate which can be used as a functional food substance and a novel drug substance via various studies in the future, little research has been conducted on Korean grapes in aspects of cultivation physiology and biotechnology to increase the content of this substance. In this connection, as a method for increasing the content of resveratrol, a method for artificially inoculating a *Plasmopara viticola* strain into grapes harvested (Korean Patent Publication No. 2003-21976), a method of treating UV-C rays on grapes after harvest (J. Argic Food Chem. 2002 Oct. 23; 50 (22): 6322-9; W00200192), or a method of treating aluminum with grapes (U.S. Pat. No. 6,834,398) are recently disclosed. However, these methods are a method of treating after harvesting or a method of a single treatment during growing grapes.

'A method for producing grapevine containing high resveratrol content using the environmental factors' is disclosed in Korean Patent Publication No. 2005-0089492 and 'Trans-resveratrol strengthened grapes increasing the content of a trans-resveratrol, a natural anti-cancer material, by infection of *Plasmopara viticola* and the method for producing them' is disclosed in Korean Patent Publication No. 2003-0021976. However, these disclosures do not describe a method of mass production of viniferin using stevioside by cell culture of grape tree tissue, unlike the present invention.

SUMMARY OF INVENTION

Technical Problem

Figure 3:
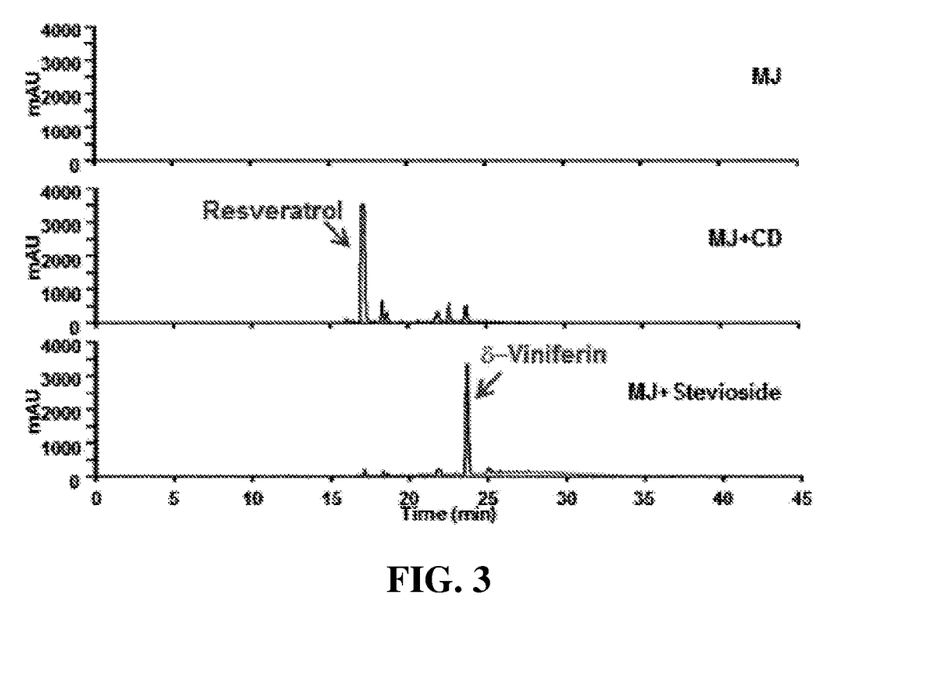
FIG. 3 is a graph for comparing the solubilization and mass production efficiency of CD-M (methyl-beta-cyclodextrin) and stevioside, which were known as solubilizing agents in the mass production of metabolites through plant liquid culture, which describes the results of HPLC analysis of resveratrol and delta-viniferin extracted after grape callus culture is treated with 100 μM MeJA and 50 mM CD-M (MJ+CD) or 100 μM MeJA and 50 mM stevioside (MJ+stevioside) and cultured. In addition, 100 μM MeJA (MJ) alone was used as a control group without treating the solubilizing agent.
Figure 5:
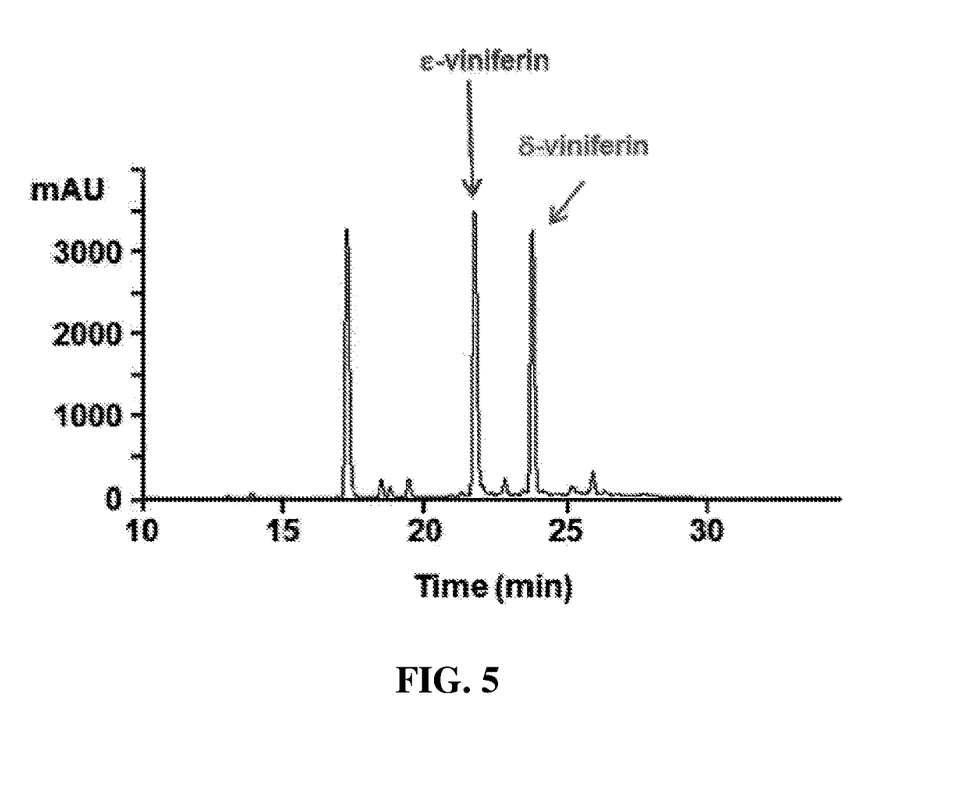
FIG. 5 illustrates the results of HPLC analysis of the production of delta-viniferin and epsilon-viniferin to which the cells are cultured in a mass-scale culture (at bioreactor level), the culture is treated with 100 μM MeJA and 50 mM stevioside, and the culture is extracted.

The present invention is derived from the demand as described above. The present inventors have attempted to construct a method for mass production of a useful substance (stilbene compound) from a callus derived from an anther tissue of the grape plant. Therefore, the anther tissue fragment of the grape plant is transplanted and cultured in a MS solid medium supplemented with the plant growth regulator to induce the callus. The induced callus is cultured in a growth medium to grow. Then, the grown callus is shaking-cultured in a liquid medium containing methyl jasmonate as an activity-inducing agent and stevioside as a solubilizing agent. The results show no production of resveratrol at the flask level and only delta-viniferin (δ-viniferin) is produced (see FIG. 3). Further, it is confirmed that the method is very efficient for the production of expensive epsilon (ε)-viniferin as well as the production of delta (δ)-viniferin at the bioreactor level, which is a condition of scale-up (see FIG. 5).

Figure 6:
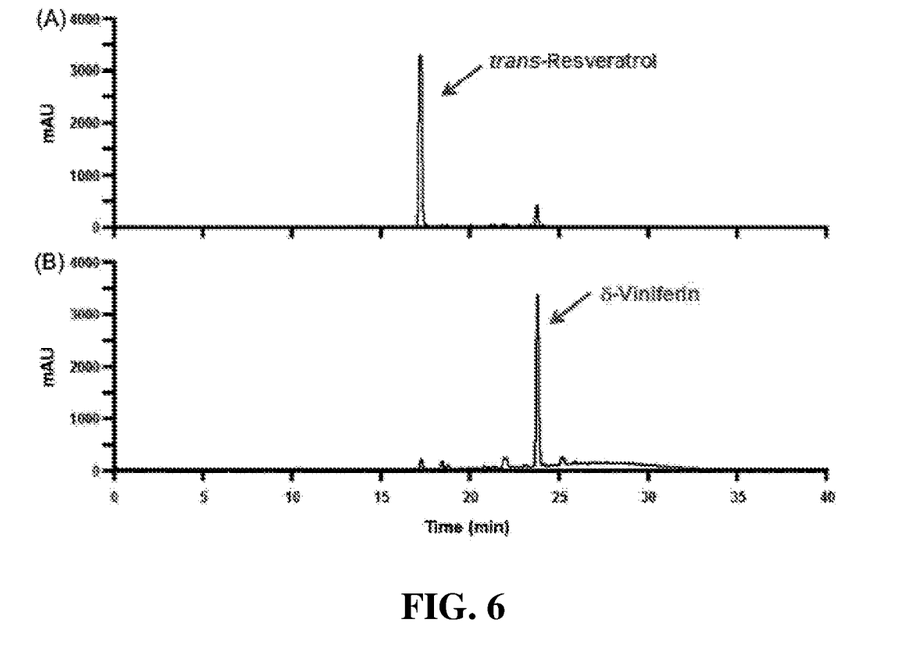
FIG. 6 illustrates the results of HPLC analysis of the production of resveratrol (A) and delta-viniferin (B) produced by a method of selectively producing resveratrol and delta-viniferin according to the present invention.

Further, when the culture medium of the grown callus is treated with an activity-inducing agent and a solubilizing agent (stevioside) and then static-cultured at the flask level, it is confirmed that only resveratrol is produced without producing viniferin (see FIG. 6A). As a result of the shaking culture, it is confirmed that only viniferin is produced without producing resveratrol (see FIG. 6B).

The present invention can provide mass production of stilbene. In particular, it is confirmed that the method of culturing callus derived from grape trees tissue using stevioside as a solubilizing agent of the present invention makes it possible to obtain not only delta (δ)-viniferin but also expensive epsilon (ε)-viniferin, thereby completing the present invention.

Solution to Problem

In order to address the issues as described above, the present invention provides a method of mass production of viniferin derived from grape trees, which includes the steps of: (a) transplanting a grape tree tissue fragment on a callus induction medium to induce a grape tree callus; (b) culturing the induced grape tree callus in a growth medium to grow; and (c) adding an activity-inducing agent and a solubilizing agent to the grown callus, followed by shaking culture.

Further, the present invention provides a composition for mass production of viniferin from a grape tree callus, which includes methyl jasmonate (MeJA) and stevioside as active ingredients.

Further, the present invention provides a method of mass production of resveratrol derived from grape trees, which includes the steps of: (a) transplanting a grape tree tissue fragment on a callus induction medium to induce a grape tree callus; (b) culturing the induced grape tree callus in a growth medium to grow; and (c) adding methyl jasmonate (MeJA) and stevioside to the grown callus, followed by static culture.

Advantageous Effects of Invention

The stilbene of the present invention has been used for health functional foods, cosmetics, medicines, dyes, functional livestock feeds, and the like due to various physiological activities such as anti-cancer, antiviral, anti-inflammation, anti-aging, and anti-oxidant. In particular, viniferin is known to be effective for protection of liver, anti-cancer, anti-oxidant, and skin whitening, have an effect of inhibiting oxidation of low-density lipoprotein and high-density lipoprotein and inhibiting the proliferation and migration of vascular smooth muscle cells. Therefore, the present invention is very useful for the mass production of viniferin among the useful substances (stilbene compounds) from a callus derived from the anther tissue of the grape plant, which is very important for the related industries.

BRIEF DESCRIPTION OF DRAWINGS

FIG. 1 illustrates the method of producing stilbene-type compounds of the present invention. p-coumaric acid is produced from an amino acid such as tyrosine or phenylalanine, and p-coumaroyl-CoA is produced by 4CL (4-coumarate: CoA ligase). The p-coumaroyl-CoA is converted to resveratrol by an STS enzyme. Two resveratrols are oxidized by oxidase, resulting in one dimer viniferin.

DESCRIPTION OF EMBODIMENTS

In order to achieve the objects of the present invention, the present invention provides a method of mass production of viniferin derived from grape trees, which includes the steps of: (a) transplanting a grape tree tissue fragment on a callus induction medium to induce a grape tree callus; (b) culturing the induced grape tree callus in a growth medium to grow; and (c) adding an activity-inducing agent and a solubilizing agent to the grown callus, followed by shaking culture.

In the method according to an aspect of the present invention, the activity-inducing agent of step (c) may be, but not limited to, methyl jasmonate, salicylic acid (SA), or flagellin 22 (Flg22), more preferably methyl jasmonate. Further, the solubilizing agent of step (c) may be, but not limited to, stevioside. The methyl jasmonate and the stevioside, respectively, may be, but not limited to, preferably added at a concentration of 50 μM to 350 μM and 40 mM to 60 mM, and more preferably 100 μM and 50 mM.

In the method according to an aspect of the present invention, the viniferin may be, but not limited to, delta (δ)-viniferin or epsilon (ε)-viniferin.

In the method according to an aspect of the present invention, the callus induction medium of step (a) may be, but not limited to, a medium containing 0.05 mg/L to 0.2 mg/L of indole-3-acetic acid (IAA), 0.05 mg/L to 0.2 mg/L of 1-naphthaleneacetic acid (NAA), 1 mg/L to 2 mg/L of 2,4-D, and 0.2 mg/L to 0.3 mg/L of kinetin as growth regulators, and preferably 0.1 mg/L of indole-3-acetic acid (IAA), 0.1 mg/L of 1-naphthaleneacetic acid (NAA), 1.5 mg/L of 2,4-D, and 0.25 mg/L of kinetin (see Table 1).

In the method according to an aspect of the present invention, the growth medium of step (b) may be, but not limited to, a Murashige & Skoog (MS) medium containing 0.5 mg/L to 2.0 mg/L of 2,4-D, and preferably a Murashige & Skoog (MS) medium containing 1 mg/L of 2,4-D.

The method according to an aspect of the present invention may, but not limited to, preferably include the steps of: (a) transplanting a sterile grape tree tissue fragment in the callus induction medium containing 0.05 mg/L to 0.2 mg/L of indole-3-acetic acid (IAA), 0.05 mg/L to 0.2 mg/L of 1-naphthaleneacetic acid (NAA), 1 mg/L to 2 mg/L of 2,4-D, and 0.2 mg/L to 0.3 mg/L of kinetin as growth regulators to induce a grape tree callus; (b) culturing the induced grape tree callus in a Murashige & Skoog (MS) medium containing 0.5 mg/L to 2.0 mg/L of 2,4-D to grow; and (c) adding 50 μM to 350 μM methyl jasmonate (MeJA) and 40 mM to 60 mM stevioside to the grown callus, followed by shaking culture, thereby mass producing delta (δ)-viniferin or epsilon (ε)-viniferin, and more preferably include the steps of: (a) transplanting a sterile grape tree tissue fragment in the callus induction medium containing 0.05 mg/L to 0.2 mg/L of indole-3-acetic acid (IAA), 0.05 mg/L to 0.2 mg/L of 1-naphthaleneacetic acid (NAA), 1 mg/L to 2 mg/L of 2,4-D and 0.2 mg/L to 0.3 mg/L of kinetin as growth regulators, followed by subculture at 23° C. to 27° C. for 25 days to 30 days to induce a grape tree callus; (b) culturing the induced grape tree callus in a Murashige & Skoog (MS) medium containing 0.5 mg/L to 2.0 mg/L of 2,4-D at 23° C. to 27° C. for 5 days to 10 days to grow; and (c) adding 100 μM methyl jasmonate (MeJA) and 50 mM stevioside to the grown callus, followed by shaking culture, thereby mass producing delta (δ)-viniferin or epsilon (ε)-viniferin.

Further, the present invention provides a composition for mass production of viniferin from a grape tree callus, the composition including methyl jasmonate (MeJA) and stevioside as active ingredients.

In the composition according to an aspect of the present invention, the methyl jasmonate and the stevioside, respectively, may be, but not limited to, preferably added at a concentration of 50 μM to 350 μM and 40 mM to 60 mM, and more preferably 100 μM and 50 mM.

In the composition according to an aspect of the present invention, the viniferin may be, but not limited to, delta (δ)-viniferin or epsilon (ε)-viniferin.

Further, the present invention provides a method of mass production of resveratrol derived from grape trees, which includes the steps of: (a) transplanting a grape tree tissue fragment on a callus induction medium to induce a grape tree callus; (b) culturing the induced grape tree callus in a growth medium to grow; and (c) adding methyl jasmonate (MeJA) and stevioside to the grown callus, followed by static culture.

The method according to an aspect of the present invention may, but not limited to, preferably include the steps of: (a) transplanting a sterile grape tree tissue fragment in the callus induction medium containing 0.05 mg/L to 0.2 mg/L of indole-3-acetic acid (IAA), 0.05 mg/L to 0.2 mg/L of 1-naphthaleneacetic acid (NAA), 1 mg/L to 2 mg/L of 2,4-D, and 0.2 mg/L to 0.3 mg/L of kinetin as growth regulators to induce a grape tree callus; (b) culturing the induced grape tree callus in a Murashige & Skoog (MS) medium containing 0.5 mg/L to 2.0 mg/L of 2,4-D to grow; and (c) adding 50 µM to 350 µM methyl jasmonate (MeJA) and 40 mM to 60 mM stevioside to the grown callus, followed by static culture.

In the method according to an aspect of the present invention, the static culture may be, but not limited to, performed at 24° C. to 26° C. for 4 days to 7 days, and preferably at 25° C. for 5 days.

The present invention is described in detail with Examples. However, the following Examples are merely illustrative of the present invention, and the contents of the present invention are not limited to the following Examples.

Example 1

In the present invention, a callus was derived from Campbell (*Vitis vinifera* L. cv Campbell Early), a representative commercial grape species. Campbell flowers were cut, washed with flowing water, and then its surface was sterilized by immersion in 70% ethanol for 1 minute. Surface sterilization was performed by placing grape flower tissues in a glass bottle on a sterile working table and using commercial bleach (about 1% sodium hypochlorite) solution for 15 minutes. They were washed three times with sterile distilled water. In the tissue completed with surface sterilization, the remaining moisture was removed using sterile filter paper, and the tissue was used for culture. The grape tissue for which the surface sterilization was completed was cut using a scalpel and each tissue (petal, anther, and filament) was transplanted on a culture medium. The medium used for the grape callus induction is shown in Table 1. The culture medium containing 0.1 mg/L of IAA, 0.1 mg/L of NAA, 1.5 mg/L of 2,4-D, and 0.25 mg/L of kinetin as growth regulators was used. The dark culture was performed in an incubator under a culture condition of 25° C. White callus produced after cultivation was subcultured in a solid medium with the same composition at intervals of about 4 weeks.

TABLE 1

| | (mg/L) |
|---|---|
| $KNO_3$ | 2,500 |
| $(NH_4)_2SO_4$ | 134 |
| $MgSO_4 \cdot 7H_2O$ | 250 |
| $MnSO_4 \cdot 1H_2O$ | 10 |
| $ZnSO_4 \cdot 7H_2O$ | 2 |
| $CuSO_4 \cdot 5H_2O$ | 0.025 |
| $NH_4H_2PO_4$ | 150 |
| $NaH_2PO_4$ | 150 |
| KCl | 300 |
| KI | 0.75 |
| $CoCl_2 \cdot 6H_2O$ | 0.025 |
| $CaCl_2 \cdot 2H_2O$ | 150 |
| $H_3BO_3$ | 3 |
| $Na_2MoO_4 \cdot 2H_2O$ | 0.25 |
| $FeSO_4 \cdot 7H_2O$ | 27.85 |
| Na2-EDTA | 37.25 |
| Thiamine HCl | 10 |
| Nicotinic acid | 1 |
| Pyridoxine HCl | 1 |
| myo-inositol | 100 |
| IAA | 0.1 |
| NAA | 0.1 |
| 2,4-D | 1.5 |
| Kinetin | 0.25 |
| Sucrose | 20,000 |
| Gelrite | 4,000 | pH = 5.8.sterilized at 121° C. for 15 minutes

Example 2. Transcription Expression Analysis of Resveratrol Biosynthesis Gene (STS, ROMT) by Cell Culture and Activity-Inducing Agent Treatment of Grape Callus In order to establish a production system of resveratrol from grape callus, transcription expression analysis was performed through a liquid culture of stabilized grape callus derived in Example 1 as described above. It was performed in which they were cultured in MS1D (4.4 g of MS, 30 g of sucrose, 0.5 g of MES, 0.1 g of Miyo-inositol, 0.4 mg thiamine HCl, and 1 mg/L of 2,4-D), which is called a Murashige & Skoog (MS) medium containing 1 mg/L of 2,4-D, liquid medium at 25° C. and 90 rpm for 7 days, followed by treatment with an activity-inducing agent. After 24 hours, total RNA was isolated from the grape callus (Kim C Y et al. 2010, *Physiologia plantarum* 139: 259-261). cDNA was synthesized from the isolated total RNA (5 µg) using First-Strand cDNA Synthesis Kit (Fermantas, Canada) as described in the instruction. The synthesized cDNA (20 µl) was diluted 2.5 times and then subjected to RT-PCR using 2 µl as a template for genes related to resveratrol and pterostilbene biosynthesis from the grape callus. PCR amplification was carried out by denaturation at 94° C. for 2 minutes, 25 cycles of at 95° C. for 30 seconds, 50° C. for 40 seconds, and 72° C. for 1 minute, and a final extension reaction at 72° C. for 10 minutes. The grape resveratrol, pterostilbene biosynthesis gene, and grapactin RT-PCR primers used for this experiment were as follows:

```
                                        (SEQ ID No: 1)
STS-F:      5'-ATGGCTTCAGTTGAGGAAATCAGA-3', (SEQ ID No: 2)
STS-R:      5'-TTAATTTGTCACCATAGGAATGCTA-3', (SEQ ID No: 3)
ROMT-F:     5'-ATGGATTTGGCAAACGGTGTGA-3', (SEQ ID No: 4)
ROMT-R:     5'-TCAAGGATAAACCTCAATGAGGGA-3', (SEQ ID No: 5)
ACTIN-F:    5'-TGCTGACAGAATGAGCAAGG-3',
and (SEQ ID No: 6)
ACTIN-R:    5'-TACTAAGAAGCTTTCAACCCAGTATA-3'.
```

Figure 1:
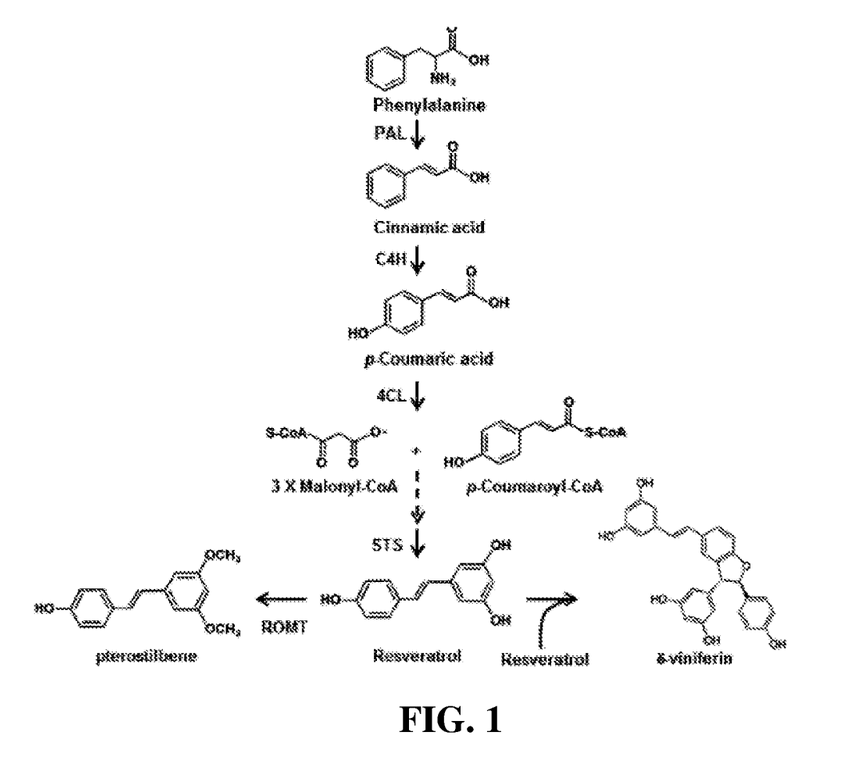
Figure 2:
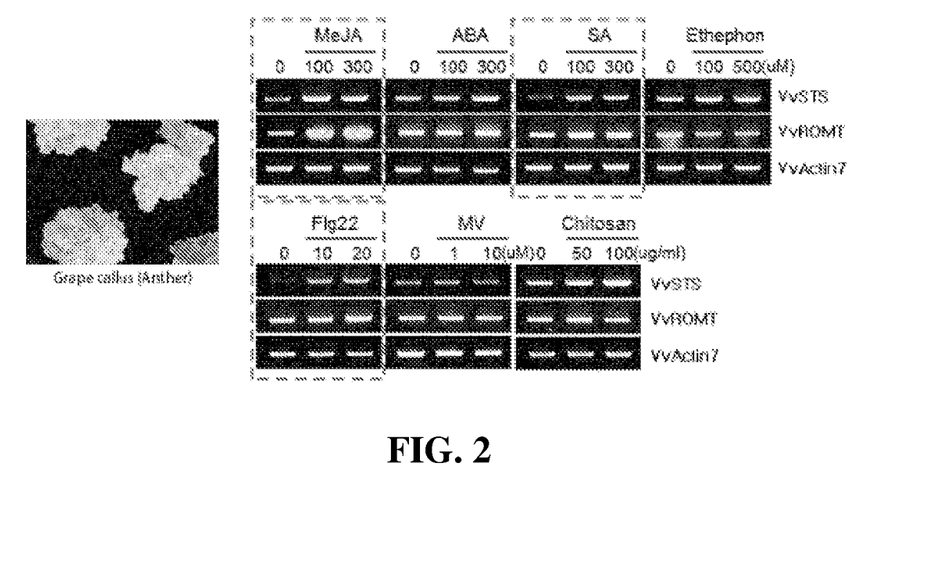
FIG. 2 illustrates the results of analysis of the transcriptional expression of resveratrol biosynthesis gene (STS, ROMT) through cell culture of grape callus and treatment with an activity-inducing agent. The activity-inducing agents used herein are methyl jasmonate (MeJA), abscisic acid (ABA), salicylic acid (SA), ethephon, flagellin 22 (Flg22), methyl viologen (MV), and chitosan.

Various activity-inducing agents were used for the treatment so as to promote the production of stilbene compound. The activity-inducing agents used herein were methyl jasmonate (MeJA), abscisic acid (ABA), salicylic acid (SA), ethephon, flagellin 22 (Flg22), methyl viologen (MV), and chitosan. The results confirmed that the expression of the two genes increased when MeJA, SA, and Flg22 were used and that the gene expression was the highest when MeJA was used (see FIG. 2).

Example 3. Treatment of Activity-Inducing Agent and Solubilizing Agent in Grape Callus Production of stilbene compounds was induced using the activity-inducing agent (100 µM MeJA) selected in Example 2 as described above. 20 ml of MS was inoculated with 2 g of grape callus, then cultured in a 125 ml flask for 7 days. Then, it was treated with 100 µM MeJA to obtain grape callus after 5 days. HPLC analysis was performed on the extract thereof. The results indicated that a trace amount of piceid was confirmed in the grape callus (data not shown).

The experiment was performed to increase the production rate by solubilizing stilbene compound produced by treating with stevioside. As described above, 7-day grape callus culture was treated with 5 mM, 10 mM, 25 mM, and 50 mM stevioside at different concentrations or was treated with 100 µM MeJA and 5 mM, 10 mM, 2 5 mM, and 50 mM stevioside at different concentrations. After 5 days of culture, the samples were separated into callus and callus culture using a filter. The separated callus was filtered, followed by dehydration. The callus was frozen with liquid nitrogen and stored at −80° C. until extraction. The callus culture extract was directly extracted from the callus culture sample without storage so as to be used.

The results demonstrated that the stilbene compound was produced most stably at a concentration of 50 mM stevioside. In order to analyze the solubilization of methyl-beta-cyclodextrin (CD-M) and stevioside, which were known as solubilizing agents, during plant tissues or cell cultures and the production efficiency of stilbene compounds, 100 µM MeJA and 50 mM of each solubilizing agent were treated, the culture was extracted, and the production tendency of stilbene compounds was examined. The results showed that trans-resveratrol was the most produced when treated with 100 µM MeJA and 50 mM CD-M, and delta-viniferin occupied most of the stilbene compounds produced when treated with 100 µM MeJA and 50 mM stevioside. Resveratrol was produced at a maximum of 40 mg/L in 100 µM MeJA and 50 mM CD-M treatment, and delta-viniferin produced at a maximum of 700 mg/L in 100 µM MeJA and 50 mM stevioside treatment (see FIG. 3)

Example 4. Bioconversion in Grape Callus

Figure 4A:
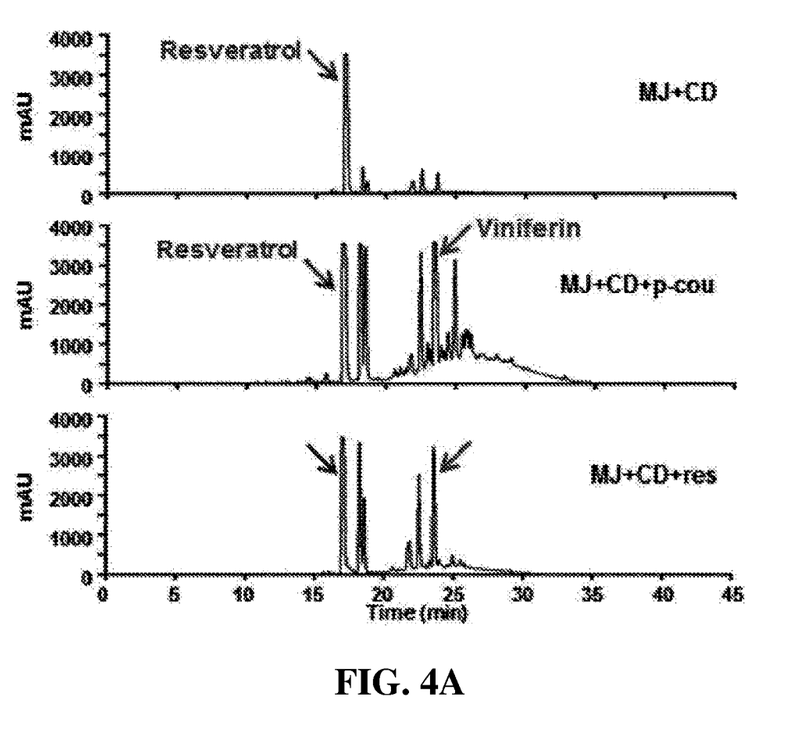
FIGS. 4A and 4B illustrate the results of the difference in bioconversion by treating grape callus culture with 100 μM MeJA and 50 mM CD-M treatment (a) or 100 μM MeJA and 50 mM stevioside (E95) treatment (b) and treating with solubilizing agents using paracumaric acid (p-cou) and resveratrol (res) as a precursor.
Figure 4B:
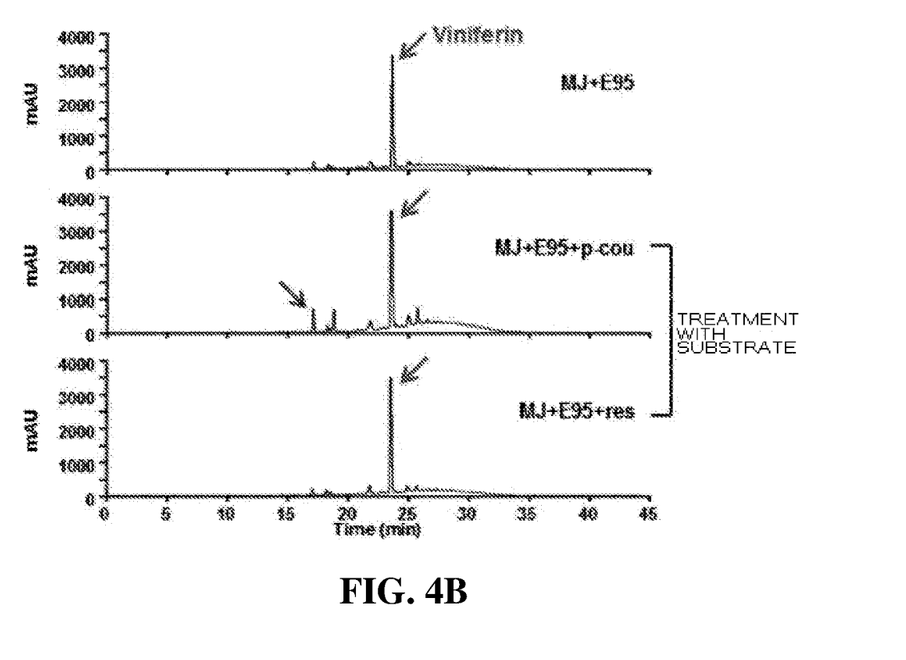

Based on the results obtained in Example 3 as described above, bioconversion was attempted using paracoumaric acid and resveratrol as a substrate in a suspension culture of grape callus. First, 100 µM MeJA and 50 mM CD-M without a substrate were used as a control group, and 2 mM paracumaric acid and resveratrol were treated with a substrate so as to be an experimental group, and the pattern thereof was confirmed (see FIG. 4A). As a result, in the case of adding a substrate, Pallidol, Parthenocissin A, Quadrangularin A, and delta-viniferin were produced in addition to resveratrol (FIG. 4A). However, 100 µM MeJA and 50 mM stevioside (E95) without a substrate were used as a control group, and 2 mM paracumaric acid and resveratrol were treated with a substrate so as to be an experimental group, and the pattern thereof was confirmed (see FIG. 4B). The results showed that delta-viniferin was largely produced in the experimental group treated with a substrate as in a control group not treated with a substrate. Based on these results, it was confirmed that when stevioside was used as a solubilizing agent in suspension culture of grape callus, the stevioside was highly effective in producing delta-viniferin (see FIGS. 4A and 4B).

Example 5. Treatment with Activity-Inducing Agent and Solubilizing Agent in Mass Culture of Grape Callus Using Bioreactor 10 g of the grape callus stabilized in Example 1 as described above was inoculated into 100 ml MS1D liquid medium in three flasks, respectively, and then cultured at 25° C. and 90 rpm for 14 days. The callus, which had been cultured for 14 days and grown, was added to a pre-sterilized and dry 3 L bioreactor. Then, 1.2 L of MS1D liquid medium was added thereto. As in Example 3, 50 mM stevioside was used with 100 µM MeJA for the treatment. After 5 days of culture, the sample was filtered to be separated into callus and callus culture. The separated callus was filtered, followed by dehydration. The callus was frozen with liquid nitrogen and stored at −80° C. until extraction. The callus culture extract was directly extracted from the callus sample without storage period so as to be used. HPLC analysis was performed on the callus extract. The results indicated that epsilon-viniferin and delta-viniferin were produced (see FIG. 5).

Example 6. Extraction of Grape Callus Culture and HPLC Analysis

The grape callus isolated in Examples 3, 4, and 5 was pulverized using liquid nitrogen. 1 g of callus powder was extracted with 3 ml of 80% methanol and then centrifuged to obtain callus extract in the upper layer thereof. Air was injected into the extracted filtrate to be dried. The dried substance was dissolved in 600 µl of 80% methanol, filtered with a 0.2 µm PTFE filter (hydrophilic, ADVANTEC, Japan), and used for HPLC analysis. 10 ml of callus culture medium was distributed and extracted into water and ethyl acetate using an equal volume of ethyl acetate, and the resulting ethyl acetate layer was dried by air injection. The dried product was dissolved in 1 ml of 80% methanol and filtered with 0.2 µm PTFE filter, and then, the resulting product was used for HPLC analysis. Agilent Technology 1200 series was used for HPLC analysis. For the analysis, four quaternary pumps were used for the pump system, an Agilent ZORBAX SB-18 (5 mm, 4.6×150 mm) was used for the column, and water (A, 0.05% trifluoroacetic acid) and acetonitrile (B 0.05% trifluoroacetic acid) were used for gradient elution for mobile phase. As a result of treatment with 100 µM MeJA and 5 mM, 10 mM, 25 mM, and 50 mM stevioside, respectively, in 7-day culture medium of the grape callus, the content of stilbene gradually increased with increasing from low concentration to high concentration of stevioside. The highest content of stilbene compound was observed at 50 mM (data not shown), and the content of the stilbene compound significantly increased compared to the group untreated with stevioside (See FIG. 3). Stilbene compounds could not be identified in the group untreated with stevioside and the callus extract.

Example 7. Isolation of Viniferin from Grape Callus and NMR Analysis

The callus culture derived from the grape anther which was treated with a solubilizing agent and prepared in Example 3 as described was separately extracted into water and ethyl acetate, thereby obtaining the ethyl acetate layer. The ethyl acetate layer obtained was concentrated under reduced pressure. The resulting concentrate (15 g) was subjected to a one-step separation using a reversed phase column (10×30 cm) using an MPLC device. In this Example, water-acetonitrile was used as an elution solvent. Seven fractions (A-G) were obtained by eluting the mixed solution of water-acetonitrile while lowering the polarity from 100:1 to 100% acetonitrile. Fraction C containing a large amount of the target compound delta-viniferin (trans-δ-viniferin as Chemical formula 1) was concentrated to obtain 1.3 g of a concentrate. 1.3 g of the concentrate obtained was subjected to reversed phase column chromatography under a mixed solvent of water and acetonitrile (2:2) using a Recycling LC device, thereby obtaining 160 mg of delta-viniferin having a purity of 80% or more. The obtained fractions were subjected to gel chromatography (Sephadex LH-20) which elutes with 95% methanol, thereby obtaining 12 mg of delta-viniferin having a purity of 98%. The structure of the obtained compound was identified using $^1$H-NMR, $^{13}$C-NMR, 2D-NMR, DEPT, and mass spectrometry.

trans-δ-Viniferin: $^1$HNMR (500 MHz, Acetone-$d_6$)d 7.45 (dd, J=8.5, 2.0 Hz, H-6), 7.27 (s, H-4), 7.25 (d, J=8.5 Hz, H-2,6A), 7.07 (d, J=16.5 Hz, H-2'), 6.92 (d, J=16.5 Hz, H-1'), 6.88 (d, J=8.1 Hz, H-7), 6.86 (d, J=8.5 Hz, H-3,5A), 6.55 (d, J=2.0 Hz, H-2,6C), 6.29 (t, J=2.0 Hz, H-2B), 6.27 (t, J=2.0 Hz, H-4C), 6.21 (d, J=2.0, H-4,6B), 5.47 (d, J=8.0 Hz, H-2), 4.48 (d, J=8.0 Hz, H-3); $^{13}$CNMR (125 MHz, Acetone-$d_6$)d 159.7 (C-7a), 158.8 (C-1,3B), 158.6 (C-3,5C), 157.5 (C-4A), 144.3 (C-5B), 139.8 (C-1C), 131.6 (C-3a), 131.2 (C-1A), 130.8 (C-5), 128.2 (C-2'), 127.7 (C-6), 127.6 (C-2,6A), 126.3 (C-1'), 123.0 (C-4), 115.2 (C-3,5A), 109.2 (C-7), 106.4 (C-4,6B), 104.7 (C-2,6C), 101.8 (C-4C), 101.4 (C-2B), 93.1 (C-2), 56.9 (C-3).

subjected to gel chromatography (Sephadex LH-20) which elutes with 95% methanol, thereby obtaining 30 mg of epsilon-viniferin having a purity of 98%. The structure of the obtained compound was identified using $^1$H-NMR, $^{13}$C-NMR, 2D-NMR, DEPT, and mass spectrometry.

trans-ε-viniferin $^1$H-NMR (400 MHz, MeOD) δ 7.14 (2H, d, J=8.0 Hz, H-2(6)a), 7.03 (2H, d, J=8.0 Hz, H-2(6)b), 6.80 (1H, d, J=13.6 Hz, H-7b), 6.78 (2H, d, J=8.0 Hz, H-3(5)a), 6.65 (2H, d, J=8.0 Hz, H-3(5)b), 6.56 (1H, d, J=13.6 Hz), 6.28 (1H, brs, H-12b), 6.21 (1H, brs, H-12a), 6.18 (2H, brs, H-10a, 14a), 5.37 (1H, d, J=8.0 Hz, H-7a), 4.35 (1H, d, J=4.0 Hz, H-8a); $^{13}$C-NMR (100 MHz, MeOD) δ 161.3 (C-11b), 158.6 (C-11a, 13a), 158.3 (C-13b), 157.1 (C-4a), 156.9 (C-4b), 146.0 (C-9a), 135.6 (C-9b), 132.5 (C-1a), 129.1 (C-1b, 7b), 127.5 (C-2(6)b), 127.0 (C-2(6)a), 122.4 (C-8b), 118.8 (C-10b), 115.1 (C-3(5)b), 115.1 (C-3(5)a), 106.3 (C-14a, 10a), 103.1 (C-14b), 101.0 (C-12a), 95.6 (C-12b), 93.5 (C-7a), 56.9 (C-8a).

[Chemical formula 1]

[Chemical formula 2]

Example 8. Isolation of Epsilon-Viniferin from Grape Callus and NMR Analysis

The callus culture derived from the grape anther which was treated with a solubilizing agent and prepared in Example 5 was separately extracted into water and ethyl acetate, thereby obtaining the ethyl acetate layer. The ethyl acetate layer obtained was concentrated under reduced pressure. The resulting concentrate (10 g) was subjected to a one-step separation using a reversed phase column (10×30 cm) using an MPLC device. In this Example, water-acetonitrile was used as an elution solvent. Five fractions (A-E) were obtained by eluting the mixed solution of water-acetonitrile while lowering the polarity from 70:1 to 100% acetonitrile. Fraction B containing a large amount of the target compound epsilon-viniferin (trans-ε-viniferin as Chemical formula 2) was concentrated to obtain 1.5 g of a concentrate. 1.5 g of the concentrate obtained was subjected to reversed phase column chromatography under a mixed solvent of water and acetonitrile (2:1) using a Recycling LC device, thereby obtaining 100 mg of epsilon-viniferin having a purity of 85% or more. The obtained fractions were

Example 9. Development of Selective Production Technology of Resveratrol and Delta-Viniferin (δ-Viniferin)

In order to mainly produce resveratrol and delta-viniferin, respectively, from the grape callus derived in Example 1 as described above, the production of the substance was induced under different conditions. 10 g of grape callus was inoculated into 100 ml of Murashige & Skoog (MS) medium containing 1 mg/L 2,4-D. Then the callus was cultured at 25° C. for 6 days at 90 rpm. They were divided into 25 ml portions and cultured for 24 hours under the same condition thereto. Then, they were treated with 100 μM MeJA and 50 mM stevioside, respectively. The callus was separated into two groups in which one group was static-cultured at 25° C. for 5 days, and the other group was cultured at 90 rpm for 5 days. Thereafter, the substance was extracted by the method of Example 6 as described above, and the extract was used for HPLC analysis. As a result of applying conditions of the different cultivation rate, resveratrol was found to be much more abundant than delta-viniferin in the static-cultured sample, and delta-viniferin was found to be much more abundant than resveratrol in the shaking-cultured sample (see FIG. 6).

The invention claimed is:

1. A method of mass production of viniferin derived from a grape tree, the method comprising the steps of:
   (a) transplanting a grape tree tissue fragment on a callus induction medium to induce a grape tree callus;
   (b) culturing the induced grape tree callus in a growth medium to grow; and
   (c) adding an activity-inducing agent and a solubilizing agent to the grown callus, followed by shaking culture,
   wherein the activity-inducing agent and the solubilizing agent in step (c) are methyl jasmonate and stevioside, respectively;
   the methyl jasmonate and stevioside are added at a concentration of 50 µM to 350 µM and 40 mM to 60 mM, respectively; and
   the viniferin is delta (δ)-viniferin or epsilon (ε)-viniferin.

2. A method of mass production of resveratrol derived from a grape tree, the method comprising the steps of:
   (a) transplanting a grape tree tissue fragment on a callus induction medium to induce a grape tree callus;
   (b) culturing the induced grape tree callus in a growth medium to grow; and
   (c) adding 50 µM to 350 µM methyl jasmonate (MeJA) and 40 mM to 60 mM stevio side to the grown callus, followed by static culture.

3. The method according to claim 2, wherein the static culture is performed at 24° C. to 26° C. for 4 days to 7 days.

* * * * *